United States Patent
Choi et al.

(10) Patent No.: US 11,432,613 B2
(45) Date of Patent: Sep. 6, 2022

(54) LOAD CELL MODULE INSERTED IN SHOES AND WEIGHT MANAGEMENT SERVICE SYSTEM USING THE SAME

(71) Applicant: Si Hyun Choi, Busan (KR)

(72) Inventors: Si Hyun Choi, Busan (KR); Hyo Jae Lee, Gimhae-si (KR); Gwang Sup Moon, Busan (KR)

(73) Assignee: Si Hyun Choi, Busan (KR)

( * ) Notice: Subject to any disclaimer, the term of this patent is extended or adjusted under 35 U.S.C. 154(b) by 560 days.

(21) Appl. No.: 16/607,389

(22) PCT Filed: Jun. 19, 2018

(86) PCT No.: PCT/KR2018/006900
§ 371 (c)(1),
(2) Date: Oct. 23, 2019

(87) PCT Pub. No.: WO2018/236123
PCT Pub. Date: Dec. 27, 2018

(65) Prior Publication Data
US 2020/0128903 A1    Apr. 30, 2020

(30) Foreign Application Priority Data
Jun. 22, 2017    (KR) .................. 10-2017-0079068

(51) Int. Cl.
*A61B 5/00* (2006.01)
*G01G 19/44* (2006.01)
(Continued)

(52) U.S. Cl.
CPC .............. *A43B 3/34* (2022.01); *A61B 5/0002* (2013.01); *A61B 5/6807* (2013.01); *G01G 19/44* (2013.01);
(Continued)

(58) Field of Classification Search
CPC .. A43B 3/34; A43B 7/00; A43B 7/144; A61B 5/002; A61B 5/6807; A61B 5/0022;
(Continued)

(56) References Cited

U.S. PATENT DOCUMENTS 7,188,439 B2 *    3/2007    DiBenedetto ........ A43B 1/0054
                                                                36/28
10,473,483 B2 *    11/2019    Jang .................... A61B 5/1036
(Continued)

FOREIGN PATENT DOCUMENTS

JP        2002-253301 A        9/2002
KR    10-2009-0091098            8/2009
(Continued)

*Primary Examiner* — Jacques M Saint Surin
(74) *Attorney, Agent, or Firm* — Rabin & Berdo, P.C.

(57) ABSTRACT

The present invention relates to a load cell module configured to be insertedly disposed in shoes and a weight management service system using the same. The load cell module comprises: a main case (10) including a load cell accommodating space (11) projected upwardly at one side thereof and a circuit and battery accommodating space (12), which are formed therein; a load cell (20) accommodated in the load cell accommodating space (11); a main PCB (30) including a tilt sensor (31) and a transmission and reception unit (32), the main PCB being accommodated in the circuit and battery accommodating space 12; and a battery (40) accommodated in the circuit and battery accommodating space 12, whereby the load cell module is detachably mounted to a heel part (H) of a midsole (M) of a shoe.

6 Claims, 4 Drawing Sheets

(51) Int. Cl.
*G01G 19/52* (2006.01)
*G09B 19/00* (2006.01)
*H02J 7/00* (2006.01)
*A43B 3/34* (2022.01)

(52) U.S. Cl.
CPC ............ *G01G 19/52* (2013.01); *G09B 19/00* (2013.01); *A61B 2560/0214* (2013.01); *A61B 2562/0252* (2013.01); *H02J 7/0045* (2013.01)

(58) Field of Classification Search
CPC ............... A61B 5/7275; A61B 5/1036; A61B 2562/0252; A61B 2562/0219; A61B 2562/0247; A61B 2560/0214; G01G 19/44; G01G 19/52; G09B 19/00; G09B 19/0038; H02J 7/0045
USPC ........................................................ 434/127
See application file for complete search history.

(56) References Cited

U.S. PATENT DOCUMENTS

| | | | |
|---|---|---|---|
| 2007/0260421 A1* | 11/2007 | Berner, Jr. | G01C 22/006 702/155 |
| 2008/0203144 A1* | 8/2008 | Kim | A61B 5/6807 235/105 |
| 2010/0090477 A1 | 4/2010 | Keating et al. | |
| 2011/0275956 A1 | 11/2011 | Son et al. | |
| 2016/0066818 A1 | 3/2016 | Cowley et al. | |
| 2016/0219968 A1* | 8/2016 | Martin | A43B 3/34 |

FOREIGN PATENT DOCUMENTS

| KR | 10-1656143 B1 | 9/2016 |
|---|---|---|
| KR | 10-1820304 B1 | 1/2018 |

* cited by examiner

LOAD CELL MODULE INSERTED IN SHOES AND WEIGHT MANAGEMENT SERVICE SYSTEM USING THE SAME

CROSS-REFERENCE TO RELATED APPLICATIONS

This application claims the benefit of Korean Patent Application No. 10-2017-0079068, filed on Jun. 22, 2017 in the Korean Intellectual Property Office, which is incorporated herein by reference in its entirety.

BACKGROUND OF THE INVENTION

1. Field of the Invention

The present invention relates to a load cell module and a weight management service system using the same, and more particularly, to a weight management service system which is configured to be insertedly disposed in a heel part of a midsole of a shoe so that variations in the weight of a wearer can be measured in real time and the measured variations in the weight can be transmitted to a mobile terminal of the wearer to control his or her weight.

2. Description of Related Art

In general, shoes are worn to protect a wearer's feet from cold or heat, and sharp materials and the like on the ground. In recent years, a variety of functional shoes are being developed which are used either to maximally exert the functions of mountaineering shoes, running shoes, golf shoes, basketball shoes, soccer shoes and the like during various sports activities depending on the intended use, or to perform therapeutic purposes such as foot disease treatment or posture correction, without being limited to simply protecting the wearer's feet.

In addition, smart shoes in which various sensors are built into shoes along with the development of a portable mobile terminal so that a wearer's body information and exercise information, including momentum, position, body weight and the like can be checked and managed through the portable mobile terminal, and a wide range of applications and management systems, and the like using the smart shoes are being actively developed.

Examples of a sensor for measuring a body weight include a load cell, a pressure gauge, a strain gauge, and various known sensors such as a piezoresistive type sensor, a piezoelectric type sensor, a capacitance type sensor, a coil type sensor and the like. However, in the case of the load cell that is widely used in a digital body weight scale for the accurate measurement of a body weight, the load cell has a length of 130 to 150 mm and a height of 30 to 40 mm, which makes it difficult to allow the load cell to be built in shoes.

As shown in FIGS. 1A and 1B, Korean Patent Registration No. 10-1656143 discloses a weight measurement device configured to be insertedly disposed in a shoe insole to enable the measurement of a body weight using a portable terminal, the device including: a main body made of a synthetic resin material ad having a space part defined therein so that gas or liquid is filled in the space part; and a control module including a signal conversion unit configured to convert an analog signal of a pressure sensor insertedly disposed in the main body into a digital signal, a storage battery configured to be supplied with power from a piezoelectric unit insertedly disposed in the main body, a control unit configured to receive the converted digital signal from the signal conversion unit to determine whether to transmit the digital signal, the control unit having an identification code inputted therein, and a wireless transmission unit configured to transmit the signal to the outside, wherein the pressure sensor and the piezoelectric unit are mounted so as to be connected to the space part and the control module including the signal conversion unit, the control unit, the wireless transmission unit, and the storage battery are insertedly disposed so as to be separated from the space part.

In the case where the pressure sensor is used to measure a wearer's body weight, measured values are different depending on the position of the pressure sensor, the posture of the wearer, the floor material on which the wearer's shoes are placed, and the like. Thus, it is essential that the wearer should input his or her weight separately and synchronize the inputted weight with the value measured by the pressure sensor. This synchronization configuration may lead to a problem.

In addition, although the inputted weight is synchronized with the measured value, there is a difference between the values measured by the same measurer depending on a tilt variation of the pressure sensor, which makes it difficult to measure an accurate body weight and a variation in the body weight.

Furthermore, when a general film type pressure sensor is insertedly disposed in shoes, there occurs a problem in that durability of the sensor is remarkably deteriorated due to a repeatedly applied load.

SUMMARY OF THE INVENTION

Accordingly, the present invention has been made to solve the aforementioned problems occurring in the prior art, and it is an object of the present invention to provide a load cell module configured to be insertedly disposed in shoes in which when a wearer's feet are level with the ground surface, an accurate variation in the body weight is detected by measuring a load applied to a load cell, and a weight management service system using a mobile terminal and an application based on variations in the weight measured by the load cell module.

To achieve the above object, in one aspect, the present invention provides a load cell module configured to be insertedly disposed in shoes, comprising: a main case including a load cell accommodating space projected upwardly at one side thereof and a circuit and battery accommodating space, which are formed therein; a load cell accommodated in the load cell accommodating space; a main PCB including a tilt sensor and a transmission and reception unit disposed thereon, the main PCB being accommodated in the circuit and battery accommodating space; and a battery accommodated in the circuit and battery accommodating space, whereby the load cell module is detachably mounted to a heel part of a midsole of a shoe.

According to another feature of the present invention, the main PCB may include a charging terminal and a functional button, which are disposed thereon so as to be exposed to a side of the main case. A weight transfer unit having a surface hardness of 10 to 60 Shore C, which is disposed on a top of the main case so as to cover an upper portion of the load cell accommodating space. In addition, the main case may include an opening formed at an upper portion thereof so as to fluidically communicate with the upper portion of the load cell accommodating space so that a weight measurement plate is disposed above the load cell in such a manner as to be protruded upwardly from the upper portion of the main case through the opening. Further, the main case may include at least two fixed projections formed on an underside thereof so as to be coupled to a concaved recess formed on the heel part of the shoe.

In another aspect, the present invention provides a weight management service system using a load cell module configured to be insertedly disposed in shoes, wherein the load cell module includes: a main case including a load cell accommodating space projected upwardly at one side thereof and a circuit and battery accommodating space, which are formed therein; a load cell accommodated in the load cell accommodating space; a main PCB including a tilt sensor and a transmission and reception unit, the main PCB being accommodated in the circuit and battery accommodating space; and a battery accommodated in the circuit and battery accommodating space, whereby the load cell module is detachably mounted to a heel part of a midsole of a shoe, the weight management service system being characterized in that when a wearer is in a state where his or her feet are level with the ground surface, the wearer's state is detected by the tilt sensor and at this time, values measured by the load cell is transmitted to a mobile terminal of the wearer in a continuous or intermittent manner through the transmission and reception unit, and variations in the measured values are outputted as graphs and figures on the mobile terminal.

Effects of the Invention

As described above, the load cell module configured to be insertedly disposed in shoes and the weight management service system using the same according to the present invention have advantageous effects in that when a wearer's feet are level with the ground surface, the measurement of his or her weight and a variation thereof using the load cell enables the accurate measurement of variations in the weight.

In addition, users can monitor variations in their weights in a continuous and real-time manner through mobile terminals based on the measured weight variations when they are eating, exercising, or doing other activities. Furthermore, the users can share the monitored variations in their weights to promote a weight management method and motivations to control their weights by themselves.

BRIEF DESCRIPTION OF THE DRAWINGS

The above and other objects, features and advantages of the present invention will be apparent from the following detailed description of the preferred embodiments of the invention when taken in conjunction with the accompanying drawings, in which.

EXPLANATION ON SYMBOLS

| | |
|---|---|
| H: heel part | M: midsole |
| 10: main case | 11: load cell accommodating space |
| 12: circuit and battery accommodating space | |
| 13: weight transfer unit | 14: fixing protrusion |
| 20: load cell | 21: weight measurement plate |
| 30: main PCB | 31: tilt sensor |
| 32: transmission and reception unit | 33: charging terminal |
| 34: functional button | 40: battery |

DETAILED DESCRIPTION OF THE PREFERRED EMBODIMENTS

Hereinafter the detailed configuration of a load cell module configured to be insertedly disposed in shoes and a weight management service system using the same according to the present invention will be described in detail with reference to the accompanying drawings.

Figure 1A:
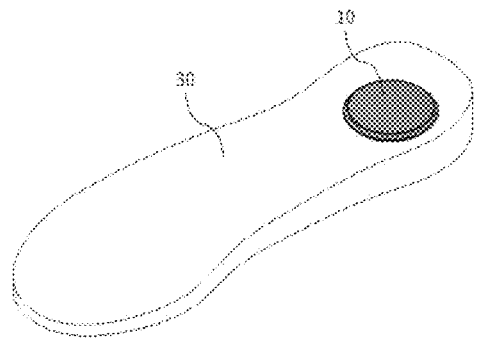
FIGS. 1A and 1B are a top perspective view and a top plan view illustrating a conventional weight measurement device configured to be insertedly disposed in a shoe insole to enable the measurement of a body weight using a portable terminal according to the prior art.
Figure 1B:
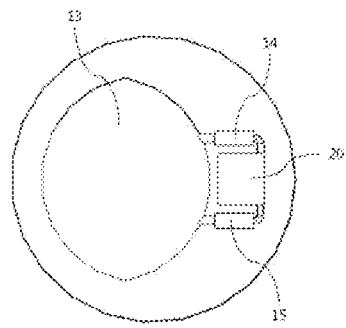
Figure 2:
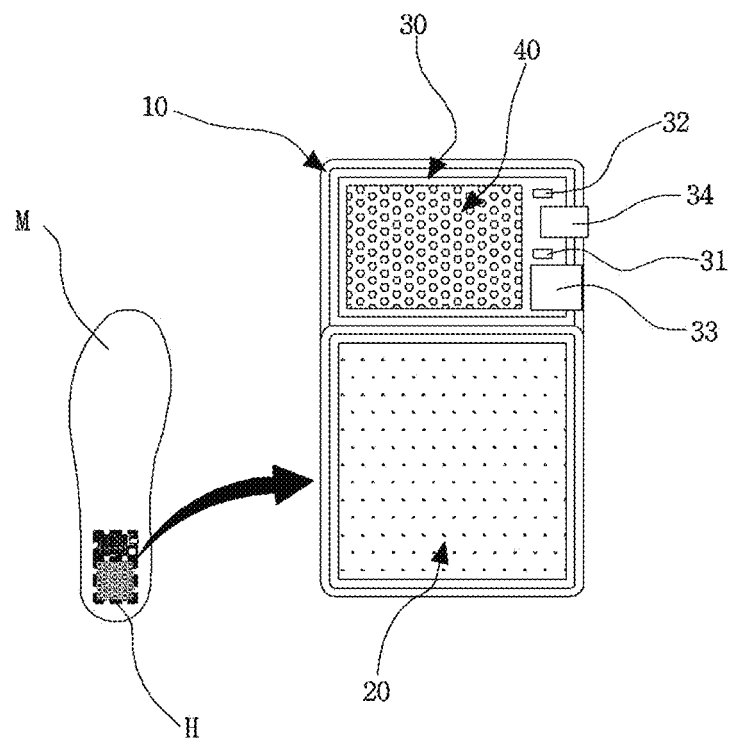
FIG. 2 is a top plan view illustrating a load cell module configured to be insertedly disposed in shoes according to the present invention.
Figure 3:
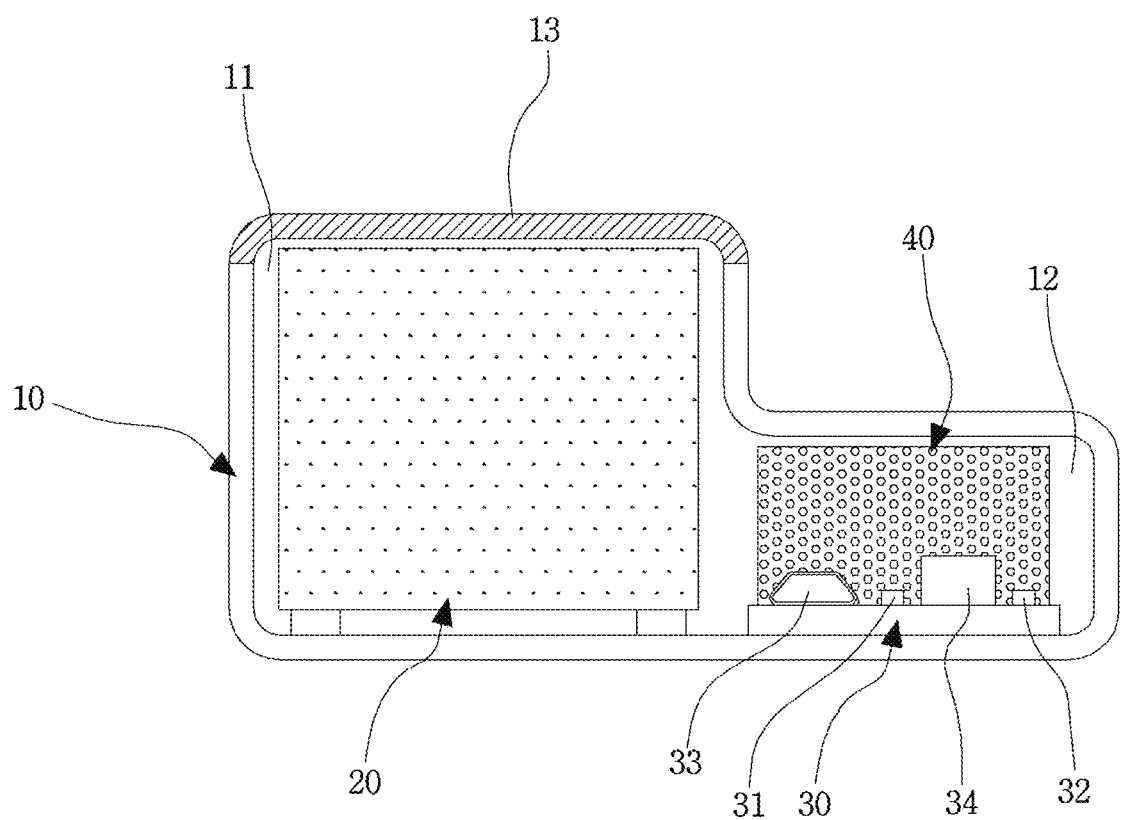
FIG. 3 is a side cross-sectional view illustrating a load cell module configured to be insertedly disposed in shoes according to a first embodiment of the present invention.

FIG. 2 is a top plan view illustrating a load cell module configured to be insertedly disposed in shoes according to the present invention, and FIG. 3 is a side cross-sectional view illustrating a load cell module configured to be insertedly disposed in shoes according to a first embodiment of the present invention.

Referring to FIGS. 2 and 3, the load cell module configured to be insertedly disposed in shoes includes: a main case 10 including a load cell accommodating space 11 projected upwardly at one side thereof and a circuit and battery accommodating space 12, which are formed therein; a load cell 20 accommodated in the load cell accommodating space 11; a main PCB 30 including a tilt sensor 31 and a transmission and reception unit 32 disposed thereon, the main PCB being accommodated in the circuit and battery accommodating space 12; and a battery 40 accommodated in the circuit and battery accommodating space 12, whereby the load cell module is detachably mounted to a heel part (H) of a midsole (M) of a shoe.

In this case, the load cell 20 has a size of about 50 mm and a height of about 20 mm into compactness so that the load cell can easily be built in shoes.

In addition, the main PCB 30 includes a charging terminal 33 and a functional button 34, which are disposed thereon so as to be exposed to a side of the main case 10.

The charging terminal 33 is connected to a USB cable to allow the battery 40 to be electrically charged, and the functional button 34 can allow for either the change of a user or the deletion of existing measured data when a shoe worn by the user is replaced with a new one.

Further, a weight transfer unit 13 having a surface hardness of 10 to 60 Shore C is disposed on a top of the main case 10 so as to cover an upper portion of the load cell accommodating space 11. In this case, the surface hardness means a Shore hardness. More specifically, the surface hardness is a value measured by a Shore hardness tester for measuring the surface hardness of a plastic material and an elastomer having an intermediate hardness using a flat cone-shaped indenter having a gradient of 35° and an elastic force of 4536 g.

Accordingly, a pressure applied by a wearer's heel can be easily delivered to the weight transfer unit 13 and the load cell 20.

More specifically, the main case 10 adopts a synthetic resin material having a relatively high hardness in order to protect the battery 40 and the main PCB 30, which are accommodated in the main case, and the weight transfer unit 13 preferably adopts a synthetic resin or rubber material having a low hardness so that a pressure can be transferred to the load cell 20. The main case 10 and the weight transfer unit 13 may be manufactured into a single piece using double injection molding, or may be manufactured separately.

Figure 5A:
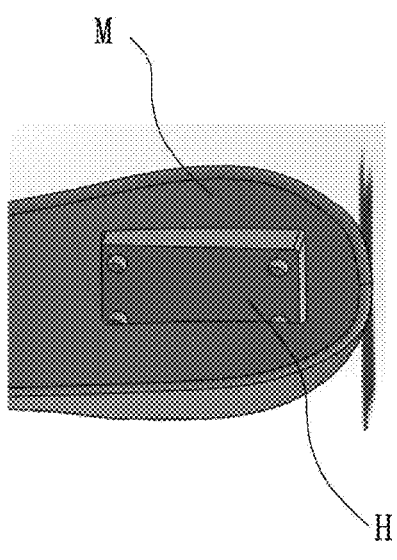
FIGS. 5A and 5B are, respectively, a perspective view illustrating a heel part of a midsole of a shoe to which a load cell module configured to be insertedly disposed in shoes according to the present invention is coupled.
Figure 5B:
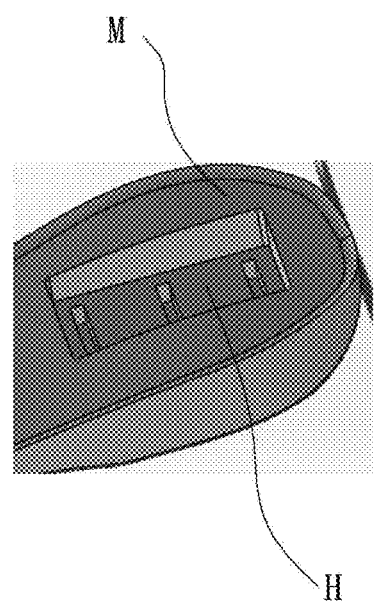

FIGS. 5A and 5B are, respectively, a perspective view illustrating a heel part of a midsole of a shoe to which a load cell module configured to be insertedly disposed in shoes according to the present invention is coupled.

Referring to FIGS. 5A and 5B, the main case (10) includes at least two fixed projections 14 formed at an underside thereof so as to be coupled to a concaved recess formed on the heel part (H) of the shoe. In the case where the load cell according to the present invention is coupled to the heel part (H), cylindrical concaved recesses may be formed on the heel part (H) of the shoe as shown in FIG. 5A, or square concaved recesses may be formed on the heel part (H) of the shoe as shown in FIG. 5B in order to ensure rigid fixation so that the load cell module can be fittingly inserted into the cylindrical or square concaved recesses. This configuration can prevent the load cell module according to the present invention from being tiltingly fixed to the heel part of the shoe.

In this case, when the surface hardness of the heel part (H) is set to be 80 Shore C or more, the load cell module can be fixed to the heel part of the shoe more rigidly.

In addition, it should be noted, of course, that the load cell module according to the present invention may include a metal or plastic case having an opening formed at an upper portion thereof to improve durability of the load cell module so that the load cell module can be inserted in the case. Moreover, the heel part (H) may be made of a metal or synthetic resin material so that damage of the load cell module can be minimized.

A method of utilizing the weight management service system using the load cell module as constructed above will be described hereinafter.

When a wearer is in a state where his or her feet are level with the ground surface, the wearer's state is detected by the tilt sensor 31 and at this time, values measured by the load cell 20 is transmitted to a mobile terminal of the wearer in a continuous or intermittent manner through the transmission and reception unit 32, and variations in the measured values are outputted as graphs and figures on the mobile terminal. When various events such as eating, exercising, walking and the like occur during the wearer's daily wearing of shoes, an accurate variation in his or her body weight can be monitored through the mobile terminal of the wearer.

Therefore, in the case where an event is performed for a brief time, variations in the body weight can be grasped in detail, and thus the weight management service system of the present invention provides effective data enabling the establishment of various plans for dietary management or body weight management including an increase or decrease in momentum.

In addition, acquaintances can share the variations in their weights through a known existing application that shares various items of exercise information together, and can give encouragement to one another, which is further effective in the weight management. Besides, acquaintances do not share the absolute values of their weights, but share the variations in their weights so that a burden on opening of their body weights to the public can be significantly reduced.

Figure 4:
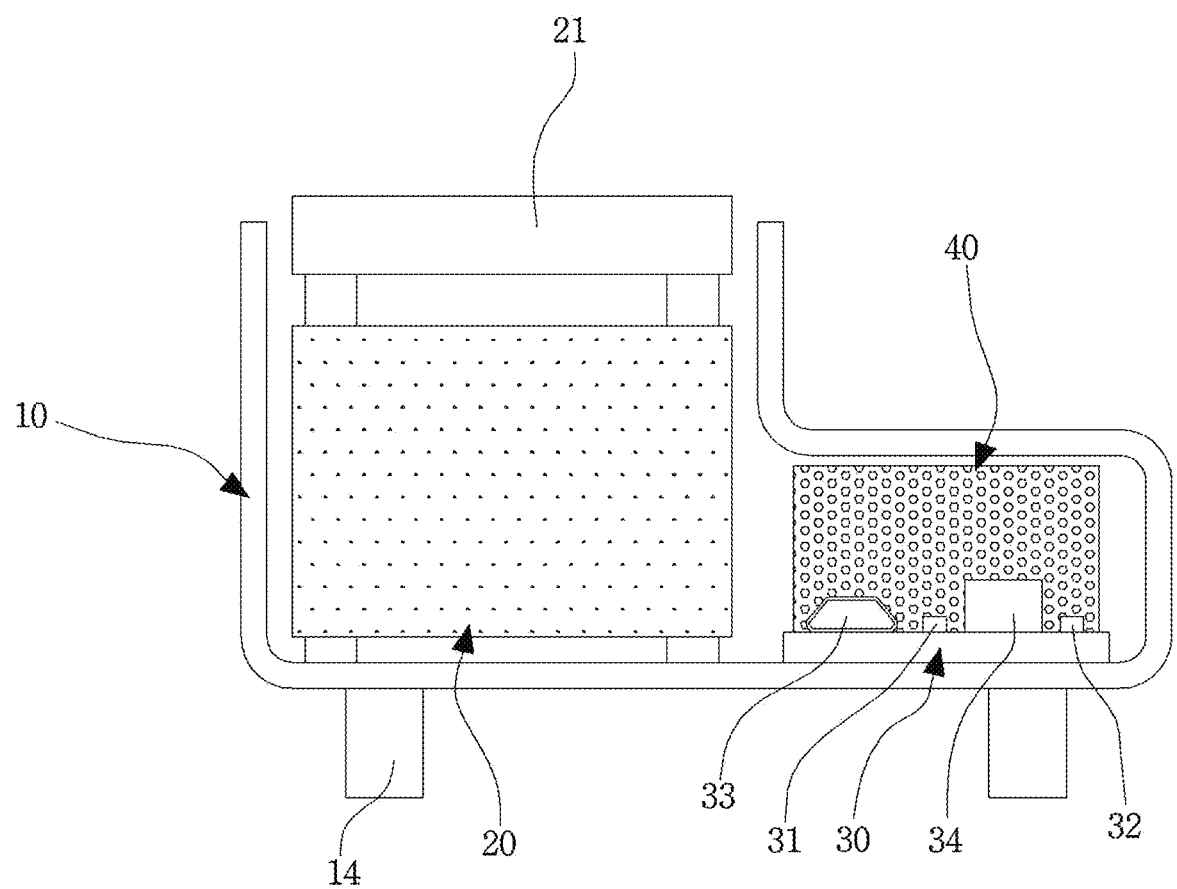
FIG. 4 is a side cross-sectional view illustrating a load cell module configured to be insertedly disposed in shoes according to a second embodiment of the present invention.

FIG. 4 is a side cross-sectional view illustrating a load cell module configured to be insertedly disposed in shoes according to a second embodiment of the present invention.

Referring to FIG. 4, the main case 10 includes an opening formed at an upper portion thereof so as to fluidically communicate with the upper portion of the load cell accommodating space 11 so that a weight measurement plate 21 as a substitute for the weight transfer unit 13 is disposed above the load cell 20 in such a manner as to be protruded upwardly from the upper portion of the main case 10 through the opening.

While the load cell module and the weight management service system using the same according to the present invention have been described and illustrated in connection with specific exemplary embodiments with reference to the accompanying drawings, it will be readily appreciated by those skilled in the art that it is merely illustrative of the preferred embodiments of the present invention and various modifications and changes can be made thereto within the spirit and scope of the present invention, set forth in the claims.

What is claimed is:

1. A load cell module configured to be insertedly disposed in shoes, comprising:
    a main case (10) including a load cell accommodating space (11) projected upwardly at one side thereof and a circuit and battery accommodating space (12), which are formed therein;
    a load cell (20) accommodated in the load cell accommodating space (11);
    a main PCB (30) including a tilt sensor (31) and a transmission and reception unit (32) disposed thereon, the main PCB being accommodated in the circuit and battery accommodating space 12; and
    a battery (40) accommodated in the circuit and battery accommodating space 12,
    whereby the load cell module is detachably mounted to a heel part (H) of a midsole (M) of a shoe.

2. The load cell module according to claim 1, wherein the main PCB (30) comprises a charging terminal (33) and a functional button (34), which are disposed thereon so as to be exposed to a side of the main case (10).

3. The load cell module according to claim 1, further comprising a weight transfer unit (13) having a surface hardness of 10 to 60 Shore C, which is disposed on a top of the main case (10) so as to cover an upper portion of the load cell accommodating space (11).

4. The load cell module according to claim 1, wherein the main case (10) comprises an opening formed at an upper portion thereof so as to fluidically communicate with the upper portion of the load cell accommodating space (11) so that a weight measurement plate (21) is disposed above the load cell (20) in such a manner as to be protruded upwardly from the upper portion of the main case (10) through the opening.

5. The load cell module according to claim 1, wherein the main case (10) comprises at least two fixed projections (14) formed on an underside thereof so as to be coupled to a concaved recess formed on the heel part (H) of the shoe.

6. A weight management service system using a load cell module configured to be insertedly disposed in shoes,
wherein the load cell module comprises:
a main case (10) including a load cell accommodating space (11) projected upwardly at one side thereof and a circuit and battery accommodating space (12), which are formed therein;
a load cell (20) accommodated in the load cell accommodating space (11);
a main PCB (30) including a tilt sensor (31) and a transmission and reception unit (32), the main PCB being accommodated in the circuit and battery accommodating space 12; and
a battery (40) accommodated in the circuit and battery accommodating space 12,
whereby the load cell module is detachably mounted to a heel part (H) of a midsole (M) of a shoe,
the weight management service system being characterized in that when a wearer is in a state where his or her feet are level with the ground surface, the wearer's state is detected by the tilt sensor (31) and at this time, values measured by the load cell (20) is transmitted to a mobile terminal of the wearer in a continuous or intermittent manner through the transmission and reception unit (32), and variations in the measured values are outputted as graphs and figures on the mobile terminal.

\* \* \* \* \*